United States Patent
Hsieh

(10) Patent No.: US 9,277,883 B2
(45) Date of Patent: Mar. 8, 2016

(54) METHOD FOR CONTROLLING GAIT-TRAINING APPARATUS USING BIOFEEDBACK

(71) Applicant: HIWIN TECHNOLOGIES CORP., Taichung (TW)

(72) Inventor: Fu-Han Hsieh, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 1 day.

(21) Appl. No.: 14/517,472

(22) Filed: Oct. 17, 2014

(65) Prior Publication Data

US 2015/0374278 A1    Dec. 31, 2015

(30) Foreign Application Priority Data

Jun. 26, 2014    (TW) ............................. 103122126 A

(51) Int. Cl.
*A63B 24/00* (2006.01)
*A61B 5/00* (2006.01)
*A61B 5/0488* (2006.01)

(52) U.S. Cl.
CPC .............. *A61B 5/486* (2013.01); *A61B 5/0488* (2013.01); *A61B 5/4836* (2013.01); *A63B 24/0062* (2013.01)

(58) Field of Classification Search
CPC .... A63B 24/00; A63B 24/0062; A61B 5/486; A61B 5/0488; A61B 5/4836
See application file for complete search history.

(56) References Cited

U.S. PATENT DOCUMENTS

| 7,857,774 | B2 | 12/2010 | Sankai | |
|---|---|---|---|---|
| 2007/0275830 | A1* | 11/2007 | Lee | A61B 5/1038 482/54 |
| 2014/0336003 | A1* | 11/2014 | Franz | A63B 22/0235 482/8 |
| 2015/0025421 | A1* | 1/2015 | Wagner | A61N 1/36025 601/2 |

* cited by examiner

*Primary Examiner* — Glenn Richman
(74) *Attorney, Agent, or Firm* — Muncy, Geissler, Olds & Lowe, P.C.

(57) ABSTRACT

A method for controlling gait-training apparatus using biofeedback is provided. A biosignal-detecting loop is used to detect and analyze the electromyographic signal of a user using the gait-training apparatus. A feedback control loop is used to drive the gait-training apparatus and determine the fatigue level of the user. When the user's muscle starts to become fatigue, the feedback control loop can further adjust the threshold for triggering the gait-training apparatus to retain the training session so that the training intensity can be regulated on-line and the user's muscle can be trained effectively based on the concept of progressive overload.

6 Claims, 4 Drawing Sheets

METHOD FOR CONTROLLING GAIT-TRAINING APPARATUS USING BIOFEEDBACK

BACKGROUND OF THE INVENTION

1. Technical Field

The present invention relates to gait-training apparatuses, and more particularly to a method for controlling a gait-training apparatus using biofeedback.

2. Description of Related Art

Progressively overloading a muscle during exercise has been recognized as an effective way to enhance the muscle strength. However, excessive overload may lead to overfatigue of the muscle and cause muscle injury. One known approach to prevent the situation is to measure and analyze the electromyographic signal of the individual to identify the fatigue level of the muscles and adjust the training intensity.

Several solutions have been proposed in the art. For instance, U.S. Pat. No. 7,857,774 disclosed a device could provide proper training by using a control unit to monitor multiple sensors simultaneously and regulate the exoskeleton based on collected data. However, this existing device uses many different types of sensors. The final product may be too expensive so that people in need may not afford this kind of rehabilitation therapy.

SUMMARY OF THE INVENTION

The primary objective of the present invention is to provide a method for controlling a gait-training apparatus using biofeedback, which refers to a median frequency shift of a user's electromyographic signal and determines the fatigue level of the user's muscles. Comparing with the prior art, the method disclosed reduces the cost and simplifies the overall procedure.

To achieve the foregoing objective, three steps were applied to the present invention. Firstly, the user's electromyographic signal is detected and analyzed in both time domain and frequency domain during gait training by a biosignal-detecting loop. Secondly, a feedback control loop is employed to drive the gait-training apparatus and determine the fatigue level of the user. In the time domain, when the electromyographic signal reaches a threshold, the feedback control loop will trigger the gait-generating loop and drive the gait-training apparatus. In the beginning, the threshold is an initial threshold. In the frequency domain, the extent of median frequency shift of the electromyographic signal is used to determine the fatigue level of the user. Thirdly, in the frequency domain, when the median frequency of the user's electromyographic signal is lower than an initial median frequency, the feedback control loop will adjust the threshold for triggering the gait-generating loop to a lower level based on the extent of median frequency shift. As a result, the user can obtain the optimal training intensity based on the concept of progressive overload and the user's muscle can be trained effectively.

Preferably, in the third step, a training effect evaluation loop is implemented to calculate the velocity of the median frequency shift of the electromyographic signal, and the velocity is used to evaluate the variation of the muscle strength of the user. Increasing of the frequency shift velocity indicates decrease of the muscle strength, where decreasing of the frequency shift velocity indicates increase of the muscle strength. When the frequency shift velocity remains still, the muscle strength is steady.

Preferably, in the first step, before the gait training is performed, a calibration process is performed to determine the initial median frequency and the initial threshold for triggering gait-generating loop of the user.

Preferably, when the median frequency of the electromyogram is lower than the preset fatigue level, the feedback control loop announces an alarm to the user.

DETAILED DESCRIPTION OF THE INVENTION

Figure 1:
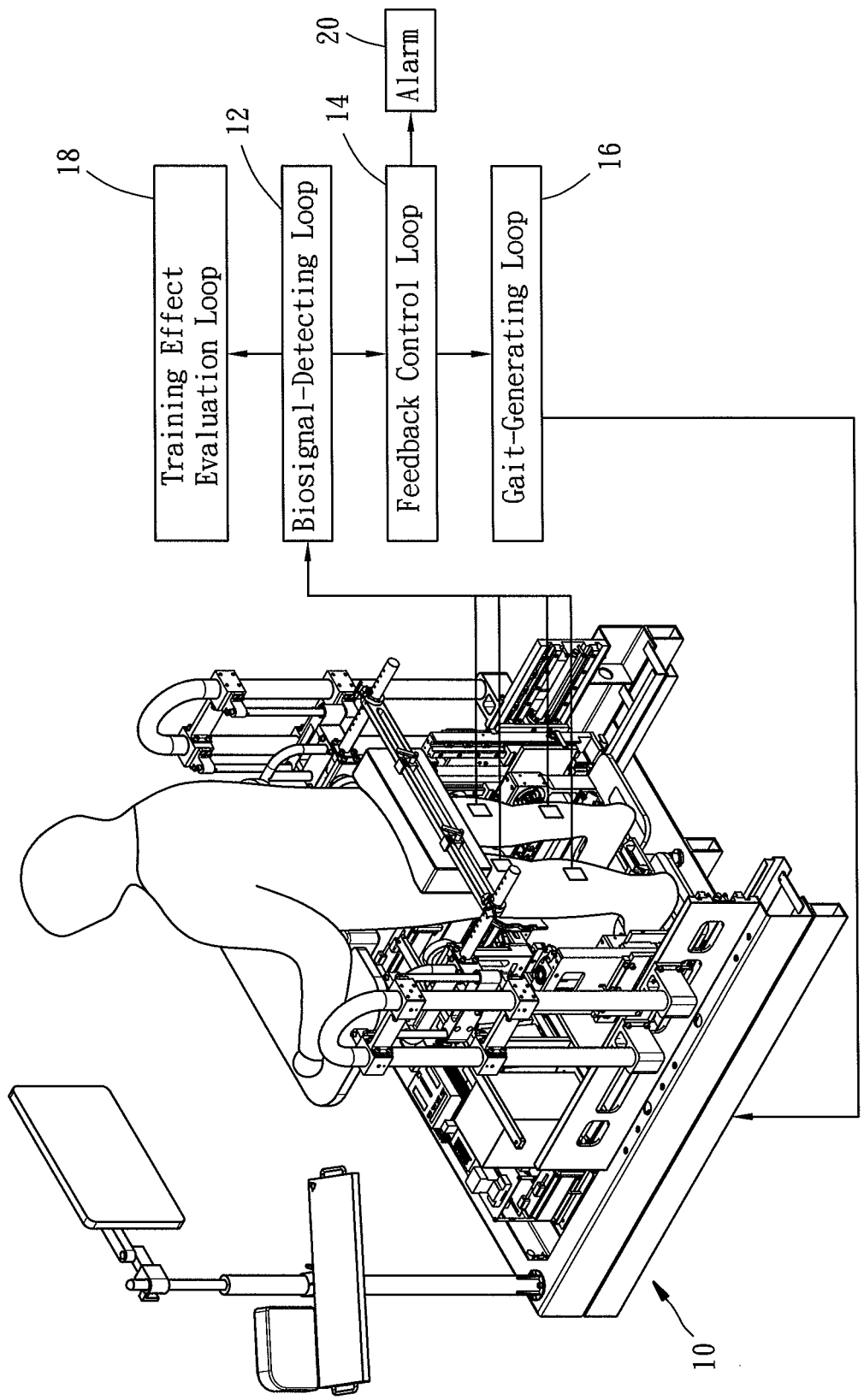
FIG. 1 is a schematic drawing showing the method of the present invention applied to a gait-training apparatus.
Figure 2:
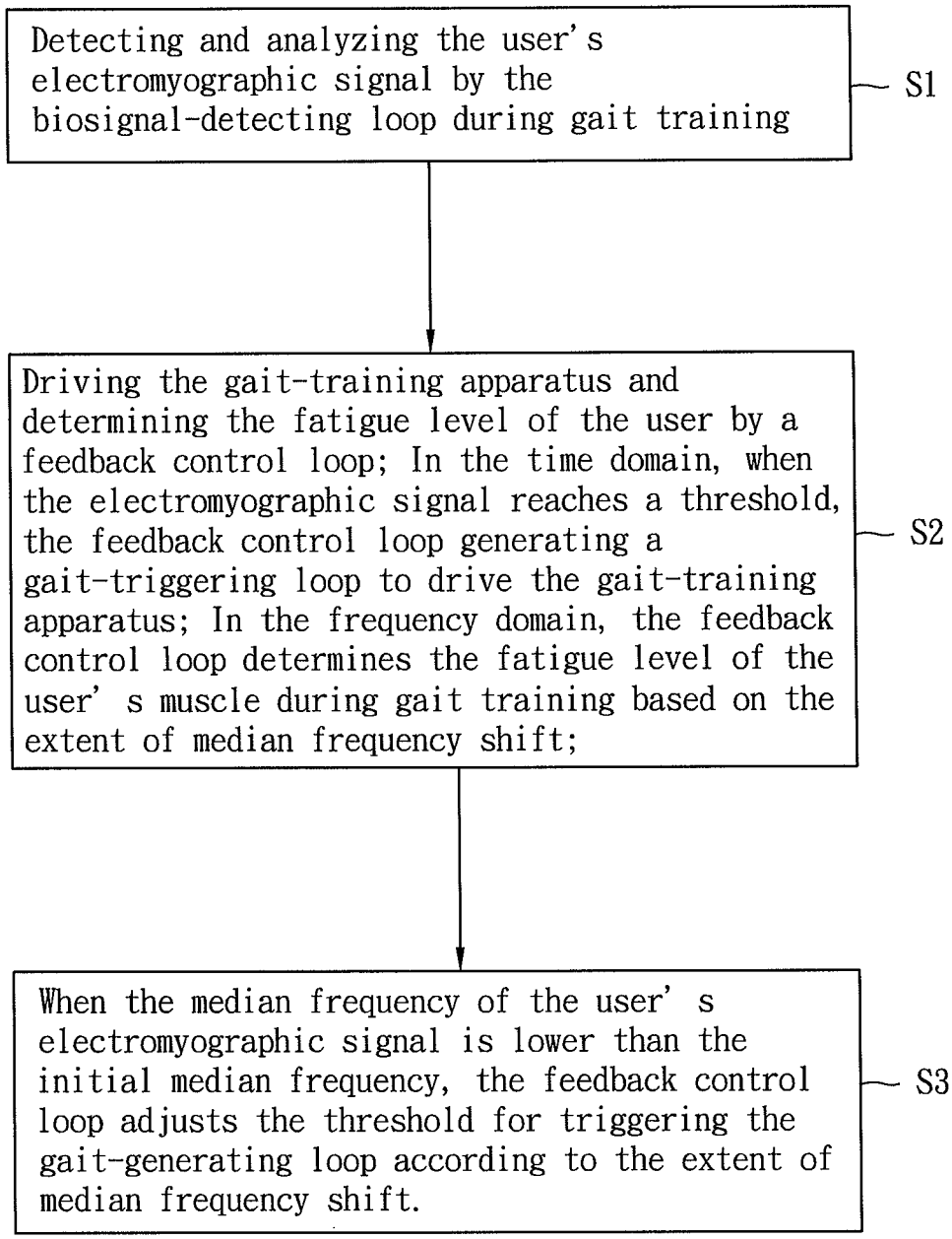
FIG. 2 is a flowchart of the method of the present invention.

Referring to FIG. 1, according to the present invention, the method primarily applied to a gait-training apparatus 10, and includes three operational steps, as shown in FIG. 2.

In step a) S1, a biosignal-detecting loop 12 is used to detect and analyze the user's electromyographic signal in both time domain and frequency domain, and performing gait training on the gait-training apparatus 10.

It should be noted that the time-domain feature of the electromyographic signal is used to calculate root mean square value (RMS) of the user's electromyogram. RMS in the time-domain feature is an index representing the strength of the muscle. On the other hand, the frequency-domain feature of the electromyographic signal is used to calculate the median frequency (MDF) of the electromyogram of the user. If the median frequency shifts to a lower frequency, the muscle starts to become fatigued.

In step b) S2, a feedback control loop 14 is used to drive the gait-generating loop 16 and determine the fatigue level of the user. In the time domain, when the electromyographic signal reaches a threshold T, the feedback control loop 14 will trigger the gait-generating loop 16 and drive the gait-training apparatus 10. In the frequency domain, the feedback control loop 14 determines the fatigue level of the user based on the extent of median frequency shift of the user's electromyographic signal.

In step c) S3, starting of the median frequency shift of the electromyographic signal indicates that the user's muscles starts to become fatigued. At this moment, the feedback control loop 14 will regulate the threshold T for triggering the gait-generating loop 16 to a lower level based on the extent of median frequency shift. The equation is as follows, $$T = T_i \times \frac{f - f_{fatigue}}{f_{normal} - f_{fatigue}}$$

where T is the preset threshold, $T_i$ is the initial threshold, $f_{normal}$ is the median frequency of the user's normal electromyographic signal, which can be obtained at the calibration session, $f_{fatigue}$ is the median frequency of the user's electromyographic signal when the user's muscles become excessively fatigued, which may be set according to the user's decision or according to the data from previous training sessions, f is the median frequency of the user's electromyographic signal during the training. In this case, the training intensity can be adjusted on-line based on the fatigue level of the user and the user's muscle can be trained effectively based on the concept of progressive overload.

Figure 3:
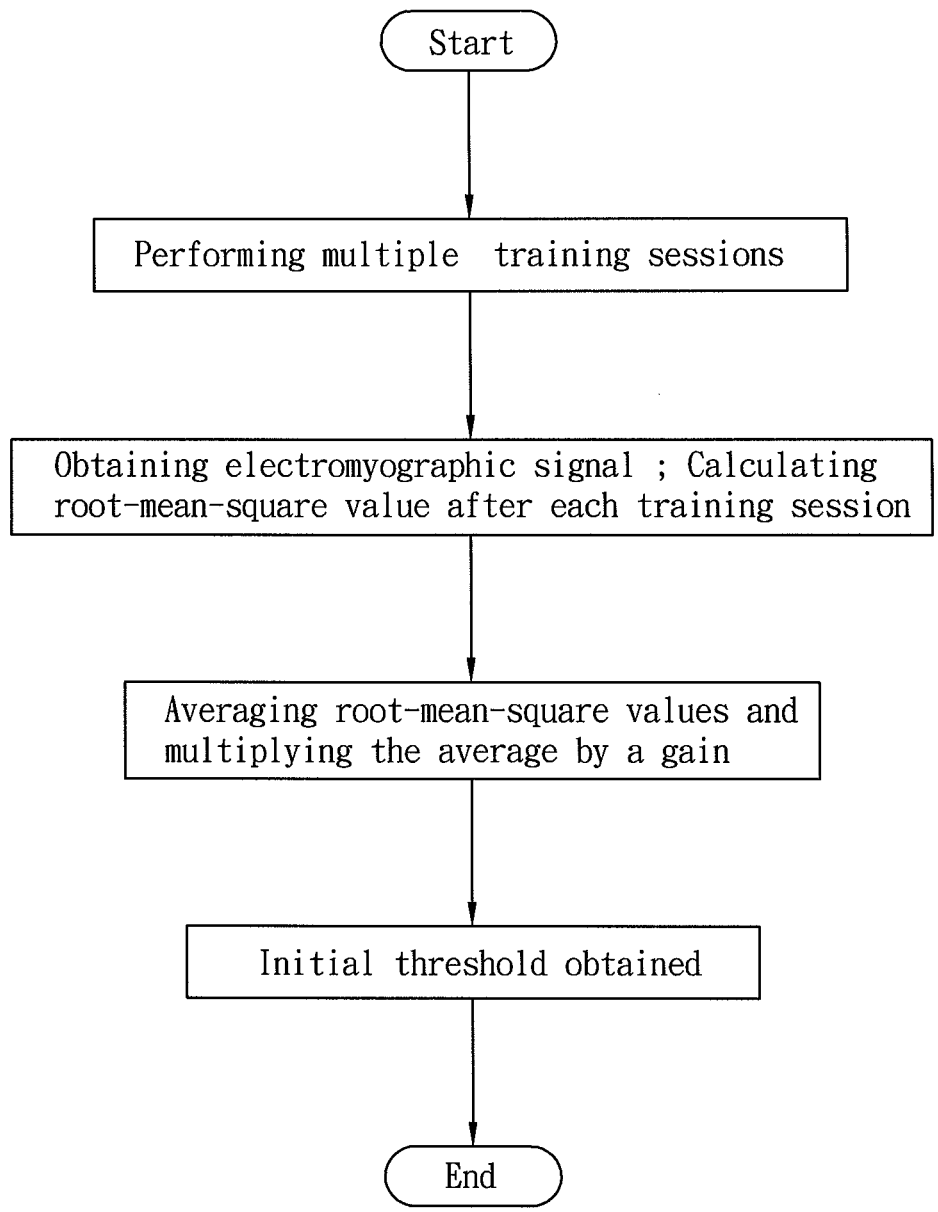
FIG. 3 is a flowchart showing the procedure to determine the initial threshold for triggering the gait-generating loop.

Because of the individual differences among users, it is necessary to calibrate the initial triggering threshold and the initial median frequency of each user. As illustrated in FIG. 3, the user performs at least five trials of gait training. The biosignal-detecting loop 12 then calculates the median frequency and the root-mean-square value of the user's electromyographic signal during each trial. The initial triggering threshold $T_i$ can be obtained by averaging the collected root-mean-square values and multiplying the result by a gain. The initial median frequency can be obtained by averaging the median frequency of each trial.

According to the aforementioned equation, the preset threshold varies with the median frequency f of the electromyographic signal throughout the training. When the median frequency f of the electromyographic signal starts to shift to a lower level, the user's muscles start to become fatigued and the amplitude of the electromyographic signal may not reach the threshold T for triggering the gait-training apparatus. At this time, the preset threshold T is lowered according to the extent of the median frequency shift to allow the gait-training apparatus 10 can still be triggered to assist the user to do exercise so that the user's muscle can obtain effective training based on the concept of progressive overload.

Figure 4:
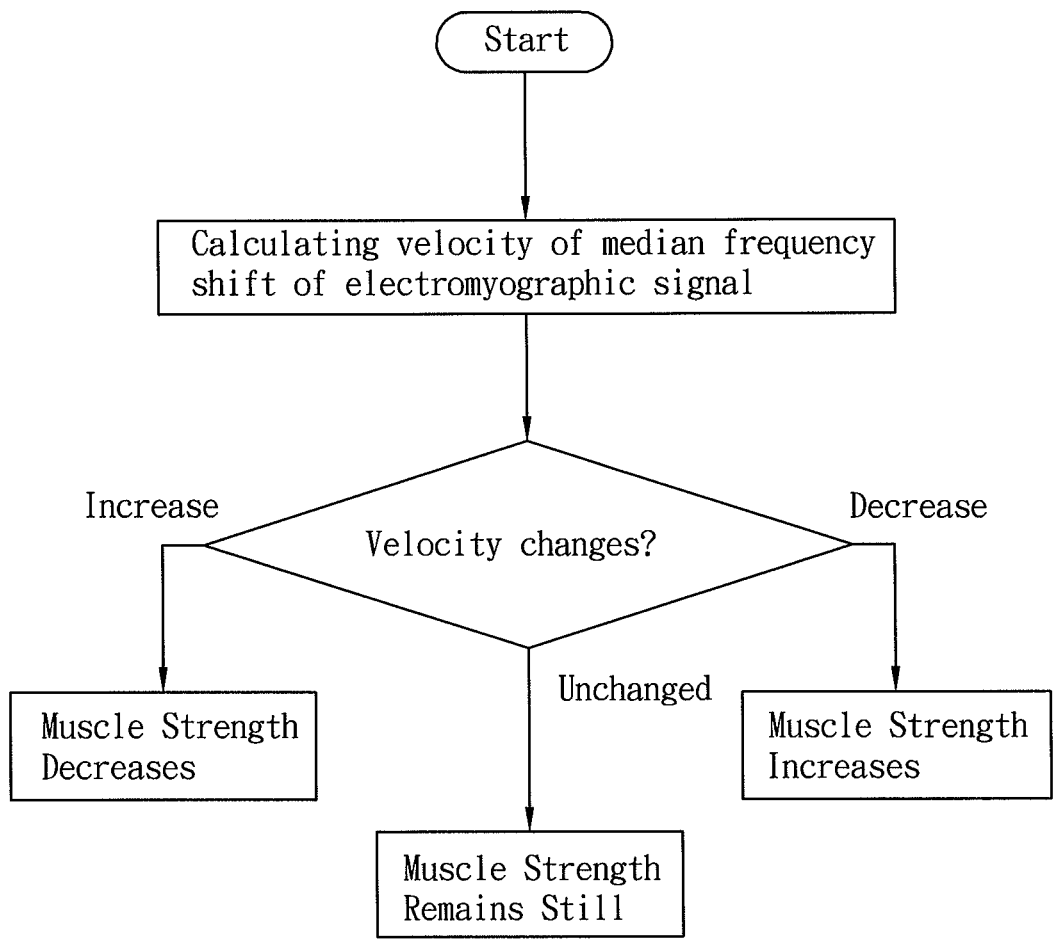
FIG. 4 is a flowchart showing the procedure of the training effect evaluation loop.

Referring to FIG. 4, in step c), a training effect evaluation loop 18 can be additionally used to calculate the velocity of median frequency f shift of the electromyogram. Increasing of the frequency shift velocity indicates decreasing of the muscle strength, where decreasing of the median frequency f shift velocity indicates increasing of the muscle strength. If the shifting velocity remains still, the muscle strength is steady. In this way, the variation of the user's muscle strength can be evaluated from session to session, and the users may know the extent of muscle strength recovery. Moreover, when the median frequency f of the electromyogram is lower than $f_{fatigue}$, the training shall be ceased immediately or the user's muscles are likely to become excessively fatigued and get injured. At this moment, the feedback control loop 14 actuates an alarm 20, as shown in FIG. 1, to announce a warning to the user to stop the training to prevent injury.

To sum up, the present invention uses the median frequency shift of the electromyogram to determine the fatigue level of the user's muscle and regulate the training intensity on-line. In addition, it is also capable of evaluating the training effect after training. Comparing with the prior art, the disclosed method requires much fewer sensors and does not need to build a large database. The cost of this kind of rehabilitation therapy could be reduced and the operation can be simplified.

What is claimed is:

1. A method for controlling a gait-training apparatus using biofeedback, comprising steps of:
   a) detecting and analyzing an electromyographic signal of a user in the time domain and the frequency domain, and performing gait training on the gait-training apparatus by using a biosignal-detecting loop;
   b) driving the gait-training apparatus and determining the user's fatigue level by a feedback control loop,
      i) in the time domain, when the electromyographic signal reaches a threshold, the feedback control loop triggers a gait-generating loop to drive the gait-training apparatus; In the beginning, the threshold is an initial threshold;
      ii) in the frequency domain, the feedback control loop determines the fatigue level of the user's muscle during gait training based on the extent of median frequency shift;
   c) When the median frequency of the user's electromyographic signal is lower than an initial median frequency, the feedback control loop adjusts the threshold for triggering the gait-generating loop according to the extent of median frequency shift.

2. The method of claim 1, wherein in step a), before the gait training is performed, the initial threshold is determined through: Performing multiple training sessions on the gait-training apparatus by the user; Obtaining a root-mean-square value of the user's electromyographic signal after each said training session by the biosignal-detecting loop; and obtaining the median frequency of the user's electromyographic signal after each said training session by the biosignal-detecting loop; and averaging the obtained root-mean-square values and multiplying the average by a gain to obtain an initial threshold; and Averaging the obtained median frequency to obtain an initial median frequency.

3. The method of claim 1, wherein in step c), further using a training effect evaluation loop to evaluate the variation of muscle strength by calculating the velocity of median frequency shift of the user's electromyographic signal.

4. The method of claim 3, wherein in step a), before the gait training is performed, the initial threshold is determined through: Performing multiple training sessions on the gait-training apparatus by the user; Obtaining a root-mean-square value of the user's electromyographic signal after each said training session by the biosignal-detecting loop; and obtaining the median frequency of the user's electromyographic signal after each said training session by the biosignal-detecting loop; and averaging the obtained root-mean-square values and multiplying the average by a gain to obtain an initial threshold; and Averaging the obtained median frequency to obtain an initial median frequency.

5. The method of claim 1, wherein step (c), the relation between preset threshold and the initial threshold is as follows, $$T = T_i \times \frac{f - f_{fatigue}}{f_{normal} - f_{fatigue}},$$

where T is the preset threshold, $T_i$ is the initial threshold, $f_{normal}$ is the median frequency of the user's electromyographic signal in normal condition, $f_{fatigue}$ is the median frequency of the user's electromyographic signal when the user's muscle is excessively fatigued, and f is the median frequency of the user's electromyographic signal during the present gait training.

6. The method of claim 1, wherein in step c), when the median frequency of the electromyographic signal is lower than $f_{fatigue}$, the feedback control loop announces an alarm.

* * * * *